United States Patent [19]
Harrison et al.

[11] 4,186,204
[45] Jan. 29, 1980

[54] ACYLAMINO DERIVATIVES

[75] Inventors: Roger G. Harrison, Farnborough; William B. Jamieson, Woking; William J. Ross, Lightwater; John C. Saunders, Maidenhead, all of England

[73] Assignees: Eli Lilly and Company; Lilly Industries Limited, both of Henrietta Pl., England

[21] Appl. No.: 8,649

[22] Filed: Feb. 1, 1979

Related U.S. Application Data

[63] Continuation of Ser. No. 848,840, Nov. 7, 1977, abandoned, which is a continuation of Ser. No. 691,965, Jun. 1, 1976, abandoned.

[30] Foreign Application Priority Data

Jun. 5, 1975 [GB] United Kingdom ............... 24221/75

[51] Int. Cl.² ..................... A61K 31/41; C07D 257/04
[52] U.S. Cl. .................................... 424/269; 424/45; 548/251
[58] Field of Search .................... 260/308 D; 424/269

[56] References Cited

U.S. PATENT DOCUMENTS

| | | | |
|---|---|---|---|
| 2,750,393 | 6/1956 | Elpern | 260/308 |
| 3,824,249 | 7/1974 | Regnier et al. | 260/308 |
| 3,929,684 | 12/1975 | Einberg | 260/2 R |

OTHER PUBLICATIONS

Derwent Abstract, 43048 W/26, week W26—12/19/75 of DT 2459380.

Primary Examiner—Frederick E. Waddell
Attorney, Agent, or Firm—Nanch J. Harrison; Everet F. Smith

[57] ABSTRACT

Acylamino tetrazolyl compounds having anti-allergic activity, methods of making the compounds and pharmaceutical formulations containing the compounds.

24 Claims, No Drawings

ACYLAMINO DERIVATIVES

This is a continuation, of application Ser. No. 848,840, filed Nov. 7, 1977, which in turn is a continuation of application Ser. No. 691,965, filed June 1, 1976, both abandoned.

This invention relates to heterocyclic chemical compounds and more particularly to certain novel 5-membered heteroaryl derivatives having nitrogen atoms as the sole heteroatoms in the ring, substituted by an acylamino group which are useful for the chemotherapy of immediate hypersensitivity conditions and/or which are useful as intermediates in preparing the active derivatives. The invention also includes processes for preparing the active compounds of the invention. Furthermore, the invention includes within its scope pharmaceutical compositions containing the pharmacologically active compounds and methods of treatment of animals, including humans, comprising administering thereto an effective dose of the compound or compounds or of pharmaceutical compositions comprising the active compound or compounds.

According to the present invention there is provided a novel heteroaryl derivative of the formula:

wherein Ar represents an optionally substituted tetrazolyl group, the acylamino group —NR$^1$COR$^2$ being attached to the carbon atom of the tetrazolyl ring, R$^1$ is C$_{1-10}$ alkyl, C$_{3-6}$ alkenyl, C$_{3-6}$ alkynyl, C$_{2-6}$ alkoxyalkyl, C$_{2-6}$ carboxyalkyl, C$_{1-6}$ haloalkyl, C$_{3-10}$ cycloalkyl, C$_{3-10}$ cycloalkyl-C$_{1-6}$ alkyl, optionally substituted phenyl-C$_{1-6}$ alkyl or optionally substituted phenyl-C$_{2-6}$ alkenyl; and R$^2$ is C$_{1-8}$ alkyl, C$_{1-6}$ haloalkyl, C$_{2-6}$ alkenyl, C$_{3-10}$ cycloalkyl, C$_{3-10}$ cycloalkyl-C$_{1-6}$ alkyl, optionally substituted phenyl, optionally substituted phenyl-C$_{1-6}$ alkyl, optionally substituted phenyl-C$_{2-6}$ alkenyl, C$_{1-4}$ alkoxycarbonyl-C$_{1-8}$ alkyl, C$_{2-8}$ carboxyalkyl or C$_{3-6}$ acyloxyalkyl; or R$^1$ and R$^2$ together form a lactam ring having 5 to 7 ring atoms.

The tetrazolyl nucleus is preferably substituted by a group selected from C$_{1-4}$ alkyl, benzyl, phenyl and halogen.

Preferred R$^1$ substituents are C$_{1-10}$ alkyl, C$_{3-6}$ alkenyl, C$_{3-8}$ cycloalkyl, and benzyl optionally substituted by halogen. Preferred R$^2$ substituents are C$_{1-8}$ alkyl, C$_{2-6}$ alkenyl, C$_{3-10}$ cycloalkyl, phenyl, benzyl, C$_{1-4}$ alkoxycarbonyl-C$_{4-8}$ alkyl, C$_{2-8}$ carboxyalkyl and C$_{3-6}$ acyloxyalkyl.

The term "C$_{1-6}$ alkyl" as used herein means a straight or branched chain alkyl group containing from 1 to 6 carbon atoms such as methyl, ethyl, isopropyl, n-butyl, s-butyl, isobutyl, t-butyl, n-amyl, s-amyl, n-hexyl, 2-ethylbutyl or 4-methylamyl.

Similarly the term "C$_{1-4}$ alkyl" as used herein means a straight or branched chain alkyl group containing from 1 to 4 carbon atoms, namely methyl, ethyl, isopropyl, n-propyl, n-butyl, isobutyl, s-butyl, t-butyl. "C$_{1-4}$ hydroxyalkyl" and "C$_{3-6}$ acyloxyalkyl" mean the aforementioned C$_{1-4}$ alkyl groups substituted with an hydroxy group and acyloxy group respectively. "C$_{2-6}$ alkoxyalkyl" and "C$_{1-6}$ haloalkyl" mean the aforementioned C$_{1-6}$ alkyl groups substituted with an alkoxy group or one or more halogen atoms, such as methoxyethyl, ethoxyethyl, ethoxybutyl, dibromomethyl, trifluoromethyl, 1-chloroethyl, 1,1-dichloroethyl, 1-iodobutyl or pentafluoroethyl.

The term "C$_{3-6}$ alkynyl" is used herein to indicate an alicyclic hydrocarbon group having 3 to 6 carbon atoms which contains a —C≡C— group. However, it should be noted that the —C≡C— group cannot be directly adjacent the nitrogen atom of the acylamino group. Similarly, C$_{3-6}$ alkenyl groups may not contain a —C=C— group directly adjacent the nitrogen atom.

"C$_{3-10}$ cycloalkyl" means a saturated ring having from 3 to 10 carbon atoms in the ring such as cyclopropyl, cyclobutyl, cyclopentyl, cyclooctyl, or adamantyl. "C$_{3-10}$ cycloalkyl-C$_{1-6}$ alkyl" means the aforementioned saturated rings attached to a C$_{1-6}$ alkylene bridge.

The term "optionally substituted phenyl" as used herein means a phenyl group unsubstituted or substituted by one or more groups which do not substantially alter the pharmacological activity of the compounds of formula (I), such as halogen, trifluoromethyl, methyl, methoxy, or nitro groups.

The term "C$_{2-6}$ carboxyalkyl" as used herein means a C$_{1-5}$ alkyl group substituted by a carboxylic acid group. Examples of such groups are carboxymethyl, carboxyethyl, carboxypropyl and carboxybutyl.

Preferred compounds are tetrazoles of structural formula:

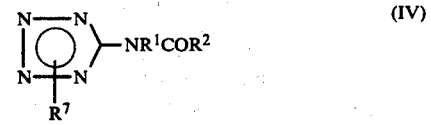

where R$^7$ is an optional substituent selected from C$_{1-4}$ alkyl and benzyl. Other tetrazoles tend to be unstable.

Particularly interesting tetrazoles of formula (IV) are those in which R$^7$ is C$_{1-4}$ alkyl, for instance methyl, attached at the 2-position of the tetrazole nucleus; R$^1$ is C$_{3-6}$ alkyl, for instance hexyl; and R$^2$ is C$_{3-6}$ cycloalkyl for instance cyclopentyl and cyclohexyl; or C$_{3-6}$ alkyl such as i-propyl.

The tetrazoles of formula (I) may be prepared by alkylating an acyl derivative of formula:

where Ar and R$^2$ are as defined previously.

Compounds of formula (VI) can be alkylated by dissolving the amide in a suitable inert, anhydrous, polar solvent such as dimethylformamide, forming an alkali metal salt thereof with an alkali metal hydride, preferably sodium hydride, and then treating the salt with an alkylating agent of formula R$^1$X$^1$ where X$^1$ is a reactive atom such as a halogen atom or a reactive group such as an alkyl sulphate group.

Of course alkylating agents and alkylating reaction conditions other then those specified above can be utilised, the nature of these being readily apparent to those acquainted with the art.

Alkylation of compounds of formula (I) in which the ring nitrogen atoms are unsubstituted may lead to the formation of mixtures of alkylated products which in certain circumstances may be difficult to separate.

The derivatives of formula (VI) can be derived from the corresponding amines of formula ArNH$_2$ by standard acylation techniques.

The amines of formula ArNH$_2$ are either known compounds, see, for example, J. Amer. Chem. Soc. 76 923 (1954) or can be prepared by modification of known synthetic methods.

The intermediates of formula (VI) are novel and are provided in a further aspect of the invention.

Compounds of formula (I) have been shown to be useful in the prophylactic and therapeutic treatment of immediate hypersensitivity diseases including asthma and in the alleviation of status asthmaticus. The compounds have low toxicity.

The compounds or compositions of the present invention may be administered by various routes and for this purpose may be formulated in a variety of forms. Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). Dosages of from 0.5 to 300 mg/kg per day, preferably 0.5 to 20 mg/kg of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of thoobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

The following Examples will further illustrate the invention.

EXAMPLE 1

N-n-Butyl-N-(2-methyltetrazol-5-yl)-2-methylpropanamide

2-Methyl-5-aminotetrazole (3.3 g, 0.033 mole) was refluxed in benzene (40 ml) with isobutyrylchloride (3.7 g) for 4 hours. After cooling and stirring at 0°–5° C. overnight, the resultant white crystalline solid was filtered off, washed with a little cold benzene and dried to yield the acylated compound (4.2 g) m.p. 120°–121° C.

This acylated compound (0.025 mole) was dissolved in dry dimethylformamide (15 ml) and added dropwise with stirring and cooling to a suspension of sodium hydride (50% oil dispersion 1.2 g, 0.025 mole) in dry dimethylformamide (10 ml). When gassing ceased, the resultant clear solution was treated dropwise with n-butyl iodide (5 g, i.e. ca. 10% excess). After 3 hours at room temperature, the mixture was poured onto ice water (100 ml) and the resultant neutral mixture extracted with diethyl ether (3×30 ml). The ether extract was dried to constant weight at 40° C./0.2 mm to give the desired compound as a colourless liquid (4.8 g).

Analysis: $C_{10}H_{19}N_5O$ requires: C 53.3; H 8.50; N 31.0%.

found: C 53.2; H 8.26; N 30.8%.

EXAMPLE 2

N-Benzyl-N-(2-methyltetrazol-5-yl)-2-methylpropanamide

The procedure of Example 1 was repeated but using benzyl bromide instead of n-butyliodide. The product after drying to constant weight at 70° C./0.5 mm, was obtained as a pale yellow oil which, on prolonged standing, became completely crystalline and had m.p. 65° C.

Analysis: $C_{13}H_{17}N_5O$ requires: C 60.2; H 6.61; N 27.0%.

found: C 60.0; H 6.41; N 26.7%.

EXAMPLE 3

N-Hexyl-N-(2-methyltetrazol-5-yl)-2-methylpropanamide

The procedure of Example 1 was repeated but using 1-iodohexane. The product was finally distilled from a Kugelrohr apparatus to give a pale yellow oil b.p. 120° C./0.1 mm.

Analysis: $C_{12}H_{23}N_5O$ requires: C 56.9; H 9.15; N 27.6%.

found: C 56.8; H 9.39; N 27.8%.

EXAMPLE 4

N-n-Butyl-N-(2-methyltetrazol-5-yl)cyclopentanecarboxamide

2-Methyl-5-aminotetrazole (9.9 g, 0.1 mole) was dissolved in warm benzene (100 ml) and cyclopentane carboxylic acid chloride (13.2 g, 0.1 mole) added dropwise to the hot solution. After gentle refluxing for 1 hour, the reaction was complete and the product was worked up as in Example 1 to give the acylated compound (17.9 g), m.p. 150° C., which in turn was alkylated as in Example 1 to yield the desired compound, after drying to constant weight, as a pale yellow liquid.

Analysis: $C_{12}H_{21}N_5O$ requires: C 57.3; H 8.42; N 27.8%.

found: C 57.6; H 8.65; N 27.6%.

EXAMPLE 5

N-Benzyl-N-(2-methyltetrazol-5-yl)cyclopentanecarboxamide

The procedure of Example 4 was repeated but using benzyl bromide in the final step; the reaction being carried out for 6 hours. The required compound obtained initially as a pale yellow oil suddenly crystallised and was recrystallised from ethyl acetate/petroleum ether 40°/60° C. 1/3 v/v—m.p. 54° C.

Analysis: $C_{15}H_{19}N_5O$ requires: C 63.1; H 6.71; N 24.6%.

found: C 63.1; H 6.59; N 24.7%.

EXAMPLE 6

N-Hexyl-N-(2-methyltetrazol-5-yl)cyclopentanecarboxamide

The procedure of Example 4 was repeated but using 1-iodohexane and reacting for 24 hours. The final product was obtained as a pale yellow liquid which was dried to constant weight at 25° C./0.1 mm.

Analysis: $C_{14}H_{25}N_5O$ requires: C 60.2; H 9.02; N 25.1%.

found: C 60.4; H 9.33; N 24.8%.

EXAMPLE 7

N-Benzyl-N-(2-benzyltetrazol-5-yl)-2-methylpropanamide

2-Benzyl-5-aminotetrazole (8.75 g, 0.05 mole) was refluxed in benzene (100 ml) with isobutyrylchloride (5.5 g) for 2 hours. Work-up as in Example 1 gave the acylated compound (9.3 g) m.p. 151°-152° C.

This acylated compound was reacted and worked-up as Example 2 to yield the desired compound, initially as a pale yellow oil, which slowly crystallised and was recrystallised from ethyl acetate/petroleum ether 40/60° C. ¼ v/v. m.p. 68° C.

EXAMPLE 8

N-n-Butyl-N-(2-benzyltetrazol-5-yl)-2-methylpropanamide

The procedure of Example 7 was repeated but using n-butyl iodide instead of benzyl bromide. The final product was dried to constant weight at 25° C./0.1 mm.

Analysis: $C_{16}H_{23}N_5O$ requires: C 63.7; H 7.69; N 23.2%.

found: C 63.9; H 8.10; N 23.2%.

EXAMPLES 9 TO 16

In a similar manner were prepared the following:

N-Methyl-N-(2-methyltetrazol-5-yl)benzamide b.p. 135°-140° C./0.1 mm (Kugelrohr).

Analysis: $C_{10}H_{11}N_5O$ requires: C 55.3; H 5.11; N 32.2%.

found: C 55.1; H 4.91; N 32.0%.

N-n-Butyl-N-(2-methyltetrazol-5-yl)cyclopropanecarboxamide b.p. 124° C./0.2 mm.

Analysis: $C_{10}H_{17}N_5O$ requires: C 53.8; H 7.68; N 31.4%.

found: C 53.7; H 7.47; N 31.3%.

N-Methyl-N-(2-methyltetrazol-5-yl)acetamide b.p. 75° C./0.07 mm. After storage gave crystals m.p. ca. 35° C.

Analysis: $C_5H_9N_5O$ requires: C 38.7; H 5.85; N 45.1%.

found: C 38.6; H 5.76; N 45.4%.

N-Allyl-N-(2-methyltetrazol-5-yl)acetamide b.p. 85° C./0.15 mm.

Analysis: $C_7H_{11}N_5O$ requires: C 46.4; H 6.12; N 38.7%.

found: C 46.1; H 6.30; N 38.8%.

N-(4-Bromobenzyl)-N-(2-methyltetrazol-5-yl)acetamide b.p. 160° C./0.15 mm (Kugelrohr).

Analysis: $C_{11}H_{12}BrN_5O$ requires: C 42.6; H 3.90; N 22.6; Br 25.8%.

found: C 42.6; H 4.16; N 22.5; Br 25.8%.

N-Methyl-N-(2-methyltetrazol-5-yl)heptanamide b.p. 118° C./0.05 mm.

Analysis: $C_{10}H_{19}N_5O$ requires: C 53.3; H 8.50; N 31.1%.

found: C 53.8; H 8.56; N 30.4%.

N-Allyl-N-(2-methyltetrazol-5-yl)heptanamide b.p. 126° C./0.05 mm.

N-Allyl-N-(2-methyltetrazol-5-yl)phenyl acetamide b.p. 140° C./0.1 mm. (Kugelrohr).

Analysis: $C_{13}H_{15}N_5O$ requires: C 60.7; H 5.88; N 27.2%.

found: C 60.8; H 5.97; N 27.0%.

The following Examples 17–23 illustrate pharmaceutical formulations containing the active compound N-n-butyl-N-(2-methyltetrazol-5-yl)cyclopentane carboxamide.

EXAMPLE 17

Soft gelatin capsules were prepared using the following ingredients:

|  | Quantity (mg/capsule) |
| --- | --- |
| Active compound | 25 |
| Propyl gallate | 0.04 |
| Fractionated Coconut Oil B.P.C. | 80 |

The above ingredients were mixed and filled into soft gelatin capsules, the main shell components of which were gelatin and glycerine.

EXAMPLE 18

Hard gelatin capsules were prepared using the following ingredients:

| | Quantity (mg/capsule) |
|---|---|
| Active compound | 28 |
| Silicon dioxide (fumed) | 25 |
| Lactose | 55 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

EXAMPLE 19

An ointment was made up from the following ingredients:

| | |
|---|---|
| Active compound | 2.2% by weight |
| Butylated hydroxyanisole B.P. | 0.05% by weight |
| White soft paraffin | q.s. 100% |

The hydroxyanisole was dissolved in the melted paraffin and the active compound then added in, and the mixture allowed to cool.

EXAMPLE 20

A topical cream containing 1% of the compound was prepared a follows:

| | grams |
|---|---|
| Active compound | 1 |
| Cetomacrogol 1000 | 3 |
| Cetostearyl alcohol | 9 |
| Liquid Paraffin | 9 |
| Butylated hydroxyanisole B.P. | 0.05 |
| Distilled Water | to 100.0 |

The active compound was mixed with the hydroxyanisole and suspended in the liquid paraffin. The cetostearyl alcohol was added and the mixture heated to 70° C. with stirring. The cetomacrogol 1000 was then dissolved in 60 g. of water heated to 70° C. The cetostearyl alcohol and liquid paraffin active compound mixture were then poured into the aqueous cetomacrogol 1000 solution with stirring and the stirring continued until the cream was cold. The cream was then made up to weight with water and passed through a stainless steel colloid mill set at a gap of 15/1000 inch.

EXAMPLE 21

Suppositories containing 30 and 60 mg. of the compound were prepared as follows:

| | |
|---|---|
| Active compound | 3 g |
| Henkel base | 97 g |

The active compound was mixed with the Henkel base which had been previously melted using the minimum amount of heat possible. The mixture was then poured into suppository moulds of a nominal capacity of 1 g. or 2 g. as desired, to produce suppositories each containing 30 mg. or 60 mg. of the active compound.

EXAMPLE 22

An aerosol was prepared containing the following ingredients:

| | Quantity per ml. |
|---|---|
| Active compound | 10.00 mg. |
| Propylene glycol | 10.00 mg. |
| Dichlorotetrafluoroethane (Propellant 114) | 550 mg. |
| Dichlorodifluoromethane (Propellant 12) | 850 mg. |

The active compound was mixed with the propylene glycol and the mix added to the propellant 114, the mixture cooled to $-15°$ to $-20°$ C. and transferred to a filling device. At the same time a mixture of propellants 114 and 12, previously cooled to $-15°$ to $-20°$ C. was fed into a second filling device. A metered amount of propellant from the second filling device was introduced into a stainless steel container, followed by the required amount of material from the first filling device. The valve units were then fitted and sealed to the container. These valve units were equipped with metering device so that approximately 0.15 mg. of the active compound is released by a single actuation of the valve.

EXAMPLE 23

Tablets were prepared using the following components:

| | |
|---|---|
| Active compound | 15.00 mg |
| Microcrystalline Cellulose | 235.00 mg. |
| Sodium Carboxymethyl Starch | 25.00 mg. |
| Magnesium Stearate | 2.5 mg. |
| Butylated Hydroxyanisole B.P. | 0.002 mg. |

The hydroxyanisole was dissolved in the active compound, the solution adsorbed onto the microcrystalline cellulose. This was mixed with the sodium carboxymethyl starch and the magnesium stearate then mixed in. Finally, the mixture was compressed to form tablets.

We claim:

1. A heteroaryl compound of the formula

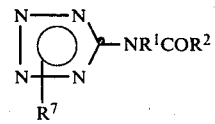

wherein $R^7$ is hydrogen, $C_{1-4}$ alkyl or benzyl; $R^1$ is $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, optionally $R^3$-substituted phenyl-$C_{1-6}$ alkyl or optionally $R^3$-substituted phenyl-$C_{2-6}$ alkenyl; $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, optionally $R^3$-substituted phenyl, $C_{1-4}$ alkoxycarbonyl-$C_{1-8}$ alkyl, $C_{2-8}$ carboxyalkyl or $C_{3-6}$ acyloxyalkyl; and $R^3$ is halogen, trifluoromethyl, methyl, methoxy or nitro.

2. A compound of claim 1 wherein $R^1$ is $C_{1-7}$ alkyl, $C_{3-6}$ alkenyl or benzyl optionally substituted by a halogen atom; $R^2$ is $C_{1-7}$ alkyl, $C_{3-8}$ cycloalkyl, or phenyl and $R^7$ is $C_{1-4}$ alkyl or benzyl.

3. A compound of claim 1 wherein $R^1$ is $C_{1-10}$ alkyl, $C_{3-6}$ alkenyl, $C_{3-8}$ cycloalkyl, or benzyl optionally substituted by a halogen atom; and $R^2$ is $C_{1-8}$ alkyl, $C_{2-6}$ alkenyl, $C_{3-10}$ cycloalkyl, phenyl, $C_{1-4}$ alkoxycarbonyl-$C_{4-8}$ carboxyalkyl, $C_{2-8}$ carboxyalkyl and $C_{3-6}$ acyloxyalkyl.

4. A compound of claim 2 wherein $R^7$ is $C_{1-4}$ alkyl attached at the 2-position of the tetrazole nucleus; $R^1$ is $C_{3-6}$ alkyl and $R^2$ is selected from $C_{3-6}$ cycloalkyl and $C_{3-6}$ alkyl.

5. A heteroaryl compound according to claim 2 being N-n-butyl-N-(2-methyltetrazol-5-yl)-2-methylpropanamide.

6. A heteroaryl compound according to claim 2 being N-benzyl-N-(2-methyltetrazol-5-yl)-2-methylpropanamide.

7. A heteroaryl compound according to claim 2 being N-hexyl-N-(2-methyltetrazol-5-yl)-2-methylpropanamide.

8. A heteroaryl compound according to claim 2 being N-n-butyl-N-(2-methyltetrazol-5-yl)-cyclopentane carboxamide.

9. A heteroaryl compound according to claim 2 being N-benzyl-N-(2-methyltetrazol-5-yl)-cyclopentane carboxamide.

10. A heteroaryl compound according to claim 2 being N-hexyl-N-(2-methyltetrazol-5-yl)-cyclopentane carboxamide.

11. A heteroaryl compound according to claim 2 being N-benzyl-N-(2-benzyltetrazol-5-yl)-2-methylpropanamide.

12. A heteroaryl compound according to claim 2 being N-allyl-N-(2-methyltetrazol-5-yl)-acetamide.

13. A heteroaryl compound according to claim 2 being N-methyl-N-(2-methyltetrazol-5-yl)-heptanamide.

14. A heteroaryl compound according to claim 2 being N-allyl-N-(2-methyltetrazol-5-yl)-heptanamide.

15. The compound of claim 2 which is N-methyl-N-(2-methyltetrazol-5-yl)benzamide.

16. The compound of claim 2 which is N-(n-butyl)-N-(2-methyltetrazol-5-yl)cyclopropanecarboxamide.

17. The compound of claim 2 which is N-(4-bromobenzyl)-N-(2-methyltetrazol-5-yl)acetamide.

18. The compound of claim 2 which is N-allyl-N-(2-methyltetrazol-5-yl)phenylacetamide.

19. A pharmaceutical formulation for the treatment of asthma comprising an amount of a compound of claim 1 which is effective for such treatment, admixed with a pharmaceutically acceptable carrier.

20. A pharmaceutical formulation of claim 19 wherein $R^1$ is selected from the group consisting of $C_{1-7}$ alkyl, $C_{3-6}$ alkenyl, and benzyl optionally substituted by a halogen atom; $R^2$ is selected from the group consisting of $C_{1-7}$ alkyl, $C_{3-8}$ cycloalkyl, and phenyl, and wherein $R^7$ is selected from $C_{1-4}$ alkyl and benzyl.

21. A pharmaceutical formulation for the treatment of asthma comprising an amount of a compound of claim 3 which is effective for such treatment, admixed with a pharmaceutically acceptable carrier.

22. A method of treating a mammal suffering from, or susceptible to, asthma which comprises administering to the mammal an amount of a compound of claim 1 wherein $R^1$ is $C_{1-7}$ alkyl, $C_{3-6}$ alkenyl or benzyl optionally substituted by a halogen atom; $R^2$ is $C_{1-7}$ alkyl, $C_{3-8}$ cycloalkyl, phenyl or benzyl; and $R^7$ is $C_{1-4}$ alkyl or benzyl which is effective for such treatment.

23. A method of treating a mammal suffering from, or susceptible to, asthma which comprises administering to the mammal an amount which is effective for such treatment of a compound of the formula

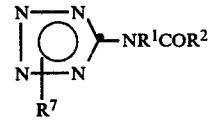

wherein $R^7$ is hydrogen, $C_{1-4}$ alkyl or benzyl; $R^1$ is $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, optionally $R^3$-substituted phenyl-$C_{1-6}$ alkyl or optionally $R^3$-substituted phenyl-$C_{2-6}$ alkenyl; $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, optionally $R^3$-substituted phenyl, optionally $R^3$-substituted phenyl-$C_{1-6}$ alkyl, optionally $R^3$-substituted phenyl-$C_{2-6}$ alkenyl, $C_{1-4}$ alkoxycarbonyl-$C_{1-8}$ alkyl, $C_{2-8}$ carboxyalkyl or $C_{3-6}$ acyloxyalkyl; and $R^3$ is halogen, trifluoromethyl, methyl, methoxy or nitro.

24. A method of treating a mammal suffering from, or susceptible to, asthma which comprises administering to the mammal a chemotherapeutically-effective amount of a compound of claim 3.

* * * * *